(12) United States Patent
Kluge

(10) Patent No.: US 10,227,371 B2
(45) Date of Patent: Mar. 12, 2019

(54) POLYMORPHS AND NEW SOLID STATES OF TIACUMICIN B

(71) Applicant: XELLIA PHARMACEUTICALS APS, Copenhagen S (DK)

(72) Inventor: Stefan Kluge, Riehen (CH)

(73) Assignee: XELLIA PHARMACEUTICALS APS, Copenhagen S (DK)

( * ) Notice: Subject to any disclaimer, the term of this patent is extended or adjusted under 35 U.S.C. 154(b) by 0 days.

(21) Appl. No.: 15/126,347

(22) PCT Filed: Mar. 17, 2015

(86) PCT No.: PCT/EP2015/055531
§ 371 (c)(1),
(2) Date: Sep. 15, 2016

(87) PCT Pub. No.: WO2015/140153
PCT Pub. Date: Sep. 24, 2015

(65) Prior Publication Data
US 2017/0081355 A1    Mar. 23, 2017

Related U.S. Application Data

(60) Provisional application No. 61/954,715, filed on Mar. 18, 2014, provisional application No. 62/020,570, filed on Jul. 3, 2014.

(51) Int. Cl.
*C07H 17/08* (2006.01)

(52) U.S. Cl.
CPC .......... *C07H 17/08* (2013.01); *C07B 2200/13* (2013.01)

(58) Field of Classification Search
CPC .............. C07H 17/08; C07B 2200/13
See application file for complete search history.

(56) References Cited

U.S. PATENT DOCUMENTS

| 4,918,174 | A | 4/1990 | McAlpine et al. |
| 7,863,249 | B2 | 1/2011 | Chiu et al. |
| 8,518,899 | B2 | 8/2013 | Chiu et al. |
| 8,722,863 | B2 | 5/2014 | Fonagy et al. |
| 9,045,515 | B2 | 6/2015 | Fonte et al. |
| 2013/0303472 | A1 | 11/2013 | Fonagy et al. |

FOREIGN PATENT DOCUMENTS

| WO | 2004014295 A2 | 2/2004 |
| WO | 2006085838 A1 | 8/2006 |
| WO | 2008091554 A1 | 1/2008 |
| WO | 2013170142 A1 | 11/2013 |

OTHER PUBLICATIONS

Kirk-Othmer Encyclopedia of Chem. Technol., pp. 95-147. (Year: 2002).*
Machine translation of CN 130275153. (Year: 2013).*
Vippagunta, S. et al "Crystalline solids" Adv. Drug Deliv. Rev., vol. 48, pp. 3-26. (Year: 2001).*
Ivanisevic, I. et al "Uses of X-ray powder diffraction . . . " Pharm. Form. Qual. , vol. Aug./Sep., pp. 30-33. (Year: 2011).*
Braga, D. et al "Crystal polymorphism . . . " Struct. Bond, vol. 132, pp. 25-50. (Year: 2009).*
Campeta, A. et al "Development of a targeted polymorph screening . . . " J. Pharm. Sci., vol. 99, No. 9, pp. 3874-3886. (Year: 2010).*
Lee, A. et al "Crystal polymorphism in chemical process . . . " Ann. Rev. Chem. Biomed. Eng., vol. 2, pp. 259-280. (Year: 2011).*
Arnone et al.; "Structure Elucidation of the Macrocyclic Antibiotic Lipiarmycin"; J. Chem. Soc., Perkin Trans. 1; pp. 13553-1359; (1987).
CN103275153 A, Sep. 4, 2013 with English Abstract, 7 pages.
International Search Report and Written Opinion; International Application No. PCT/EP2015/055531; International Filing Date Mar. 18, 2014; dated Jun. 15, 2015; 16 pages.
JP Application No. 2016-558001; Translation of Decision of Rejection, dated Jul. 27, 2018; 3 pages.
JP Application No. 2016-558001; Translation of Decision of Rejection, Drafted Date Jul. 27, 2018; 3 pages.
K. Serizawa, et al., "Polymorphism of Drugs and Science of Crystallization"; Maruzen Planet Co., Ltd.; Sep. 20; pp. 272-317; (2002).
M. Matsuoka, Foundation and Application of Crystal Polymorphism; CMC Publishing Co., Ltd., Oct. 22, 1st edition, pp. 105-117 and 181-191; (2010).

\* cited by examiner

*Primary Examiner* — Leigh C Maier
(74) *Attorney, Agent, or Firm* — Cantor Colburn LLP

(57) ABSTRACT

The present invention relates to new polymorphs consisting in crystallines solvates of Tiacumicin B, the solvates being propanol, isopropanol, acetic acid, isopropyl acetate, chlorobenzene and methyl-ethyl-ketone. The present invention also relates to a new amorphous form of Tiacumicin B.

2 Claims, 22 Drawing Sheets

XRPD of the starting material:

XRPD of amorphous material:

XRPD of the chlorobenzene crystal solvate in table format.

| Angle [°2Θ] | d value [Å] | Intensity [Cps] | Intensity % |
|---|---|---|---|
| 3.32 | 26.6 | s | 34.2 |
| 6.66 | 13.3 | vs | 91.5 |
| 7.27 | 12.1 | m | 29.9 |
| 7.78 | 11.4 | m | 17.1 |
| 9.94 | 8.9 | m | 27.9 |
| 10.75 | 8.2 | w | 10.9 |
| 11.48 | 7.7 | w | 14.0 |
| 11.73 | 7.5 | m | 18.4 |
| 12.61 | 7.0 | w | 14.1 |
| 12.85 | 6.9 | m | 23.4 |
| 13.25 | 6.7 | m | 17.3 |
| 13.65 | 6.5 | m | 16.4 |
| 14.13 | 6.3 | w | 12.5 |
| 14.65 | 6.0 | m | 16.5 |
| 15.10 | 5.86 | m | 20.3 |
| 15.58 | 5.68 | w | 13.6 |
| 16.23 | 5.46 | m | 21.9 |
| 16.97 | 5.22 | s | 49.1 |
| 17.59 | 5.04 | w | 10.1 |
| 18.20 | 4.87 | w | 10.7 |
| 18.77 | 4.72 | vs | 100.0 |
| 19.93 | 4.45 | s | 44.4 |
| 20.34 | 4.36 | w | 13.8 |
| 20.77 | 4.27 | s | 31.3 |
| 22.03 | 4.03 | m | 24.5 |
| 22.41 | 3.96 | w | 12.4 |
| 22.67 | 3.92 | w | 13.5 |
| 23.05 | 3.86 | m | 19.9 |
| 23.55 | 3.77 | w | 14.5 |
| 24.50 | 3.63 | w | 12.9 |
| 25.29 | 3.52 | w | 8.8 |
| 25.83 | 3.45 | w | 11.3 |
| 26.63 | 3.34 | w | 8.8 |
| 27.09 | 3.29 | w | 9.0 |
| 27.51 | 3.24 | w | 8.0 |
| 28.51 | 3.13 | w | 10.3 |
| 30.07 | 2.97 | w | 10.1 |
| 31.43 | 2.84 | w | 8.6 |
| 31.75 | 2.82 | w | 7.0 |
| 32.79 | 2.73 | w | 9.8 |
| 33.43 | 2.68 | w | 6.3 |

FIG. 2B

XRPD of the n-propanol crystal solvate in table format:

| Angle [°2θ] | d value [Å] | Intensity [Cps] | Intensity % |
|---|---|---|---|
| 3.32 | 26.6 | s | 49.6 |
| 7.51 | 11.8 | vs | 79.2 |
| 7.70 | 11.5 | s | 43.7 |
| 9.94 | 8.9 | m | 21.3 |
| 10.54 | 8.4 | m | 17.8 |
| 10.64 | 8.3 | m | 23.1 |
| 11.93 | 7.4 | m | 15.4 |
| 12.17 | 7.3 | m | 20.0 |
| 13.26 | 6.7 | w | 12.9 |
| 13.97 | 6.3 | m | 20.3 |
| 14.30 | 6.2 | m | 26.2 |
| 14.44 | 6.1 | m | 20.1 |
| 14.87 | 5.95 | w | 12.5 |
| 15.39 | 5.75 | s | 30.7 |
| 15.79 | 5.61 | s | 32.4 |
| 16.52 | 5.36 | w | 10.6 |
| 16.80 | 5.27 | m | 15.4 |
| 17.33 | 5.11 | w | 10.2 |
| 18.76 | 4.73 | vs | 100.0 |
| 19.04 | 4.66 | w | 14.4 |
| 19.38 | 4.58 | w | 13.9 |
| 19.91 | 4.46 | s | 43.2 |
| 20.21 | 4.39 | m | 29.4 |
| 21.13 | 4.20 | m | 17.2 |
| 21.71 | 4.09 | w | 12.8 |
| 22.52 | 3.94 | m | 15.9 |
| 23.00 | 3.86 | m | 15.1 |
| 24.05 | 3.70 | w | 13.1 |
| 24.40 | 3.65 | w | 13.6 |
| 24.89 | 3.57 | w | 11.5 |
| 25.23 | 3.53 | w | 10.7 |
| 26.65 | 3.34 | w | 7.7 |
| 28.71 | 3.11 | w | 10.9 |
| 29.23 | 3.05 | w | 8.8 |
| 30.04 | 2.97 | w | 7.5 |
| 30.66 | 2.91 | w | 9.1 |
| 32.74 | 2.73 | w | 8.6 |
| 34.83 | 2.57 | w | 8.3 |

FIG. 3B

XRPD of the iso-propanol crystal solvate in table format:

| Angle | d value | Intensity | Intensity % |
|---|---|---|---|
| 2-Theta° | Angstrom | Cps | % |
| 3.35 | 26.4 | w | 8.1 |
| 6.49 | 13.6 | s | 56.1 |
| 7.78 | 11.4 | w | 5.5 |
| 9.88 | 8.9 | s | 32.9 |
| 10.04 | 8.8 | w | 8.5 |
| 11.46 | 7.7 | m | 22.4 |
| 12.59 | 7.0 | m | 25.1 |
| 12.83 | 6.9 | w | 8.0 |
| 13.36 | 6.6 | vw | 3.5 |
| 13.66 | 6.5 | w | 5.5 |
| 14.39 | 6.1 | w | 6.4 |
| 15.57 | 5.69 | vw | 3.3 |
| 15.86 | 5.58 | vw | 4.9 |
| 16.45 | 5.39 | m | 21.7 |
| 16.78 | 5.28 | w | 5.8 |
| 17.66 | 5.02 | vw | 3.7 |
| 18.64 | 4.76 | vs | 100.0 |
| 18.94 | 4.68 | w | 13.2 |
| 19.38 | 4.58 | vw | 4.6 |
| 19.79 | 4.48 | s | 37.5 |
| 20.04 | 4.43 | w | 5.7 |
| 20.50 | 4.33 | m | 19.8 |
| 21.15 | 4.20 | vw | 4.2 |
| 21.67 | 4.10 | w | 6.6 |
| 22.15 | 4.01 | w | 13.0 |
| 22.68 | 3.92 | w | 8.1 |
| 22.99 | 3.87 | w | 6.3 |
| 23.28 | 3.82 | w | 6.3 |
| 23.45 | 3.79 | vw | 4.9 |
| 24.03 | 3.70 | vw | 4.9 |
| 24.54 | 3.62 | vw | 3.2 |
| 25.29 | 3.52 | w | 5.6 |
| 25.81 | 3.45 | vw | 3.3 |
| 28.31 | 3.15 | w | 7.6 |
| 28.91 | 3.09 | vw | 3.4 |
| 29.21 | 3.06 | vw | 4.7 |
| 29.41 | 3.03 | vw | 3.9 |
| 29.91 | 2.98 | w | 5.2 |
| 30.93 | 2.89 | vw | 2.6 |
| 31.98 | 2.80 | vw | 3.8 |
| 32.63 | 2.74 | vw | 2.9 |
| 34.61 | 2.59 | vw | 3.0 |
| 37.80 | 2.38 | vw | 2.3 |
| 38.40 | 2.34 | vw | 4.0 |

FIG. 4B

XRPD of the MEK crystal solvate in table format:

| Angle [°2Θ] | d value [Å] | Intensity [Cps] | Intensity % |
|---|---|---|---|
| 3.32 | 26.6 | s | 55.6 |
| 7.48 | 11.8 | vs | 100.0 |
| 8.38 | 10.5 | m | 29.2 |
| 9.94 | 8.9 | s | 32.0 |
| 10.48 | 8.4 | s | 34.0 |
| 10.62 | 8.3 | s | 38.8 |
| 11.89 | 7.4 | m | 26.7 |
| 12.13 | 7.3 | s | 32.9 |
| 12.81 | 6.9 | m | 28.6 |
| 13.23 | 6.7 | m | 25.2 |
| 14.29 | 6.2 | s | 32.5 |
| 15.72 | 5.63 | s | 51.9 |
| 16.81 | 5.27 | m | 25.5 |
| 18.06 | 4.91 | m | 24.1 |
| 18.61 | 4.76 | s | 64.2 |
| 18.88 | 4.70 | m | 25.7 |
| 19.75 | 4.49 | s | 37.7 |
| 20.07 | 4.42 | m | 29.0 |
| 21.00 | 4.23 | m | 29.9 |
| 21.71 | 4.09 | m | 21.9 |
| 22.12 | 4.01 | m | 22.0 |
| 22.55 | 3.94 | m | 29.3 |
| 22.92 | 3.88 | m | 20.7 |
| 23.99 | 3.71 | m | 20.8 |
| 24.34 | 3.65 | m | 18.6 |
| 30.50 | 2.93 | w | 13.8 |
| 34.80 | 2.58 | w | 10.5 |

FIG. 5B

XRPD of the acetic acid crystal solvate in table format:

| Angle [°2Θ] | d value [Å] | Intensity [Cps] | Intensity % |
|---|---|---|---|
| 3.32 | 26.6 | s | 46.1 |
| 6.71 | 13.2 | vs | 87.1 |
| 7.07 | 12.5 | s | 44.3 |
| 7.57 | 11.7 | vs | 88.1 |
| 7.96 | 11.1 | s | 33.6 |
| 9.93 | 8.9 | s | 46.9 |
| 10.09 | 8.8 | s | 38.9 |
| 10.59 | 8.3 | s | 30.1 |
| 11.52 | 7.7 | s | 36.8 |
| 11.66 | 7.6 | m | 28.5 |
| 12.15 | 7.3 | m | 29.9 |
| 12.80 | 6.9 | s | 50.5 |
| 13.47 | 6.6 | m | 25.8 |
| 14.04 | 6.3 | m | 28.7 |
| 14.30 | 6.2 | s | 32.5 |
| 15.92 | 5.56 | s | 46.9 |
| 16.53 | 5.36 | m | 27.4 |
| 16.88 | 5.25 | s | 35.8 |
| 18.11 | 4.90 | m | 23.6 |
| 18.69 | 4.74 | vs | 100.0 |
| 19.01 | 4.67 | s | 30.4 |
| 19.89 | 4.46 | vs | 76.8 |
| 20.19 | 4.40 | s | 30.7 |
| 20.69 | 4.29 | m | 26.6 |
| 21.12 | 4.20 | m | 27.8 |
| 22.02 | 4.03 | m | 24.7 |
| 22.35 | 3.97 | s | 35.4 |
| 23.12 | 3.84 | m | 28.2 |
| 23.62 | 3.76 | m | 21.7 |
| 24.21 | 3.67 | m | 20.3 |
| 24.44 | 3.64 | m | 19.9 |
| 25.32 | 3.52 | m | 18.8 |
| 27.65 | 3.22 | w | 14.0 |
| 28.62 | 3.12 | m | 17.5 |

FIG. 6B

Glass transition temperature of high purity amorphous Tiacumicin material by using Fox Equation:

| %H2O | Tg (°C) | Tg(K) | RH(%) |
|------|---------|-------|-------|
| 0.0% | 113 | 386 | 0% |
| 0.5% | 108 | 381.4 | 6% |
| 1.0% | 104 | 376.9 | 13% |
| 1.5% | 100 | 372.5 | 19% |
| 2.0% | 95 | 368.2 | 26% |
| 2.5% | 91 | 364.0 | 32% |
| 3.0% | 87 | 359.9 | 39% |
| 3.5% | 83 | 355.9 | 45% |
| 4.0% | 79 | 352.0 | 51% |
| 4.5% | 75 | 348.2 | 58% |
| 5.0% | 71 | 344.4 | 64% |
| 5.5% | 68 | 340.7 | 71% |
| 6.0% | 64 | 337.1 | 77% |
| 6.5% | 61 | 333.6 | 84% |
| 7.0% | 57 | 330.2 | 90% |
| 7.5% | 54 | 326.8 | 96% |
| 8.0% | 50 | 323.5 | 103% |

XRPD in table format of Tiacumicin solvate form α.

| Angle 2-Theta ° | d value Angstrom | Intensity rel | Intensity % % |
|---|---|---|---|
| 3,40 | 26,0 | w | 6,2 |
| 7,12 | 12,4 | vs | 93,3 |
| 8,48 | 10,4 | vw | 2,0 |
| 10,16 | 8,7 | w | 10,0 |
| 10,31 | 8,6 | m | 20,7 |
| 10,78 | 8,2 | w | 13,6 |
| 11,65 | 7,6 | w | 14,6 |
| 12,47 | 7,1 | m | 21,9 |
| 13,71 | 6,5 | w | 7,6 |
| 13,95 | 6,3 | w | 9,2 |
| 14,47 | 6,1 | w | 6,8 |
| 14,77 | 5,99 | w | 11,1 |
| 15,72 | 5,63 | w | 5,2 |
| 16,66 | 5,32 | s | 40,3 |
| 18,70 | 4,74 | vs | 100,0 |
| 18,97 | 4,68 | w | 7,2 |
| 19,90 | 4,46 | s | 47,9 |
| 20,38 | 4,36 | w | 9,7 |
| 20,89 | 4,25 | w | 6,9 |
| 21,08 | 4,21 | w | 10,1 |
| 21,63 | 4,11 | w | 11,3 |
| 22,03 | 4,03 | m | 16,1 |
| 22,42 | 3,96 | vw | 4,9 |
| 22,97 | 3,87 | w | 7,7 |
| 23,38 | 3,80 | w | 10,9 |
| 23,78 | 3,74 | w | 5,9 |
| 24,51 | 3,63 | w | 7,5 |
| 25,09 | 3,55 | w | 9,2 |
| 25,33 | 3,51 | vw | 4,4 |
| 26,00 | 3,42 | vw | 4,2 |
| 26,38 | 3,38 | vw | 4,2 |
| 27,31 | 3,26 | vw | 1,6 |
| 27,63 | 3,23 | vw | 1,9 |
| 28,54 | 3,13 | w | 7,6 |
| 28,73 | 3,10 | w | 6,2 |
| 31,90 | 2,80 | vw | 2,9 |
| 32,78 | 2,73 | vw | 4,9 |
| 35,02 | 2,56 | vw | 3,6 |

FIG. 8C

XRPD in table format of Tiacumicin solvate form β.

| Angle 2-Theta ° | d value Angstrom | Intensity rel. | Intensity % |
|---|---|---|---|
| 3,28 | 26,9 | w | 5,9 |
| 4,91 | 18,0 | w | 6,6 |
| 6,51 | 13,6 | vw | 4,1 |
| 7,32 | 12,1 | m | 17,2 |
| 9,79 | 9,0 | w | 7,9 |
| 10,59 | 8,3 | w | 9,8 |
| 11,46 | 7,7 | vw | 2,6 |
| 13,63 | 6,5 | vw | 2,8 |
| 15,28 | 5,79 | vw | 4,3 |
| 15,68 | 5,65 | m | 24,4 |
| 16,61 | 5,33 | w | 5,5 |
| 18,82 | 4,71 | vs | 100,0 |
| 19,10 | 4,64 | vw | 4,1 |
| 19,44 | 4,56 | vw | 4,3 |
| 19,95 | 4,45 | w | 8,8 |
| 20,21 | 4,39 | m | 26,9 |
| 21,80 | 4,07 | w | 5,0 |
| 22,64 | 3,92 | w | 5,8 |
| 23,32 | 3,81 | w | 6,1 |
| 28,80 | 3,10 | vw | 4,7 |
| 29,33 | 3,04 | vw | 3,2 |

FIG. 9C

POLYMORPHS AND NEW SOLID STATES OF TIACUMICIN B

CROSS REFERENCE TO RELATED APPLICATIONS

This application is a National Stage Application of PCT/EP2015/055531, filed Mar. 17, 2015, which claims the benefit of U.S. Provisional Application No. 61/954,715 filed on Mar. 18, 2014 and 62/020,570 filed on Jul. 3, 2014, all of which are incorporated by reference in their entirety herein.

The present invention relates to new polymorphs and new solid states of Tiacumicin B. Tiacumicin B can be produced as disclosed in U.S. Pat. No. 4,918,174 or WO2004014295. There are several publications mentioning various polymorphs and crystals related to tiacumicins e.g. U.S. Pat. No. 8,722,863, U.S. Pat. No. 7,863,249, U.S. Pat. No. 8,518,899, CN103275153, J. Chem. Soc. Perkin Trans, by Arnone and Nasini, 1987, page 1353-1359.

The following background is based on Florence et al, Physiochemical Principles of Pharmacy, $5^{th}$ edition, August 2011:

The physical properties of the solid state seen in crystals and powders of both drugs and pharmaceutical excipients are of interest because they can affect both the production of dosage forms and the performance of the finished product.

Crystalline solids can exist in several subphases, such as polymorphs, solvates, hydrates, and cocrystals. Polymorphs are different crystalline forms (at different free energy states) of the same compound. On the other hand, solvates, hydrates and co-crystals are similar in that they comprise a stoichiometric or significant amount of an additional compound. E.g., a drug together with an organic solvent (to form a solvate) or water (to form a hydrate), or another crystalline solid (to form co-crystals). Both types of compounds participate in the short-range and long-range orders of the crystal and therefore these subphases are regarded as single crystalline forms consisting of two types of molecules.

The nature of the crystalline form of a drug substance may affect its stability in the solid state, its solution properties and its absorption.

The solid state is important for a variety of reasons: morphology, particle size, polymorphism, solvation or hydration can affect filtration, flow, tableting, dissolution and bioavailability. The crystals of a given substance may vary in size, the relative development of the given faces and the number and kind of the faces (or forms) present; that is, they may have different crystal habits. The habit describes the overall shape of the crystal in rather general terms and includes, for example, acicular (needle-like), prismatic, pyramidal, tabular, equant, columnar and lamellar types.

A more fundamental difference in properties may be found when the compounds crystallise as different polymorphs. When polymorphism occurs, the molecules arrange themselves in two or more different ways in the crystal; either they may be packed differently in the crystal lattice or there may be differences in the orientation or conformation of the molecules at the lattice sites. These variations cause differences in the X-ray diffraction patterns of the polymorphs and this technique is one of the main methods of detecting the existence of polymorphs. The polymorphs have different physical and chemical properties; for example, they may have different melting points and solubilities and they also usually exist in different habits.

Polymorphism is common with pharmaceutical compounds, but predictability of the phenomenon is difficult. Its pharmaceutical importance depends very much on the stability and solubility of the forms concerned. It is difficult, therefore, to generalise, except to say that where polymorphs of insoluble compounds occur there are likely to be biopharmaceutical implications.

The term "polymorph" as used herein is meant to embrace crystalline solid states of a pure compound including solvates, co-crystals and crystals.

However, polymorphs also have different crystal lattices and consequently their energy contents may be sufficiently different to influence their stability and biopharmaceutical behaviour.

The most important consequence of polymorphism is the possible difference in the bioavailability of different polymorphic forms of a drug; particularly when the drug is poorly soluble. The rate of absorption of such a drug is often dependent upon its rate of dissolution. The most stable polymorph has the lowest solubility and slowest dissolution rate and consequently often a lower bioavailability than the metastable polymorph. It has been proposed that when the free energy differences between the polymorphs are small there may be no significant differences in their biopharmaceutical behaviour as measured by the blood levels they achieve.

When some compounds crystallise they may entrap solvent in the crystal. Crystals that contain a solvent as part of the crystal lattice are called crystal solvates, or crystal hydrates when water is the solvent of crystallisation. Crystals that contain no water of crystallisation are termed anhydrates. Crystal solvates exhibit a wide range of behaviour depending on the interaction between the solvent and the crystal structure. With some solvates the solvent plays a key role in holding the crystal together; for example, it may be part of a hydrogen-bonded network within the crystal structure. These solvates are very stable and are difficult to desolvate. When these crystals lose their solvent they may collapse and re-crystallise in a new crystal form. We can think of these as polymorphic solvates. In other solvates, the solvent is not part of the crystal bonding and merely occupies voids in the crystal. These solvates lose their solvent more readily and desolvation does not destroy the crystal lattice.

Certain impurities can inhibit the growth pattern and favour the growth of metastable polymorphs. Impurities in a crystallization process have been found to have vast effects on the morphology of the resulting crystal, with both beneficial and detrimental effects possible for the resultant product.

Impurities occur because materials are never 100% pure. An impurity compound can often be incorporated at a regular site in the crystal structure.

BRIEF DESCRIPTION OF THE FIGURES

FIG. 2B: XRPD of the chlorobenzene crystal solvate of Tiacumicin B in table format showing the relative intensity of the peaks, highest peak=100. The peaks are designated w for weak intensity, m for medium intensity, s for strong intensity and vs for very strong intensity.

FIG. 3B: XRPD of the n-propanol crystal solvate of Tiacumicin B in table format showing the relative intensity of the peaks, highest peak=100. The peaks are designated w for weak intensity, m for medium intensity, s for strong intensity and vs for very strong intensity.

FIG. 4B: XRPD of the isopropanol crystal solvate of Tiacumicin B in table format showing the relative intensity of the peaks, highest peak=100. The peaks are designated w for weak intensity, m for medium intensity, s for strong intensity and vs for very strong intensity.

FIG. 5B: XRPD of the methyl-ethyl-ketone crystal solvate of Tiacumicin B in table format showing the relative intensity of the peaks, highest peak=100. The peaks are designated w for weak intensity, m for medium intensity, s for strong intensity and vs for very strong intensity.

FIG. 6B: XRPD of the acetic acid crystal solvate of Tiacumicin B in table format showing the relative intensity of the peaks, highest peak=100. The peaks are designated w for weak intensity, m for medium intensity, s for strong intensity and vs for very strong intensity.

FIG. 8C: XRPD in table format of Tiacumicin solvate form α.

FIG. 9C: XRPD in table format of Tiacumicin solvate form β.

A 4.6×150 mm Agilent Zorbax Eclipse XDB-C8 3.5 μm column was used and the detector wavelength was 230 nm. A flow rate of 1.0 mL/min was used. Injection volume was 10 μL and a total runtime of 21 min. The gradient program was 0 min: 60% A, 40% B. 3 min; 50% A, 50% B, 14 min 39% A, 61% B, 14.5 60% A, 40% B until 21 min.

Mobile Phase A: 2.0 mL of trifluoroacetic acid was added to 2 L of Milli-Q water.

Mobile Phase B: 1.0 mL of trifluoroacetic acid was added to 2 L of acetonitrile.

App 0.2 mg of high purity Tiacumicin material was scaled into a HPLC vial and diluted with citric buffer at pH 4.0+−0.1 that has been mixed with Acetonirile at a ratio of 2:3.

Figure 11:
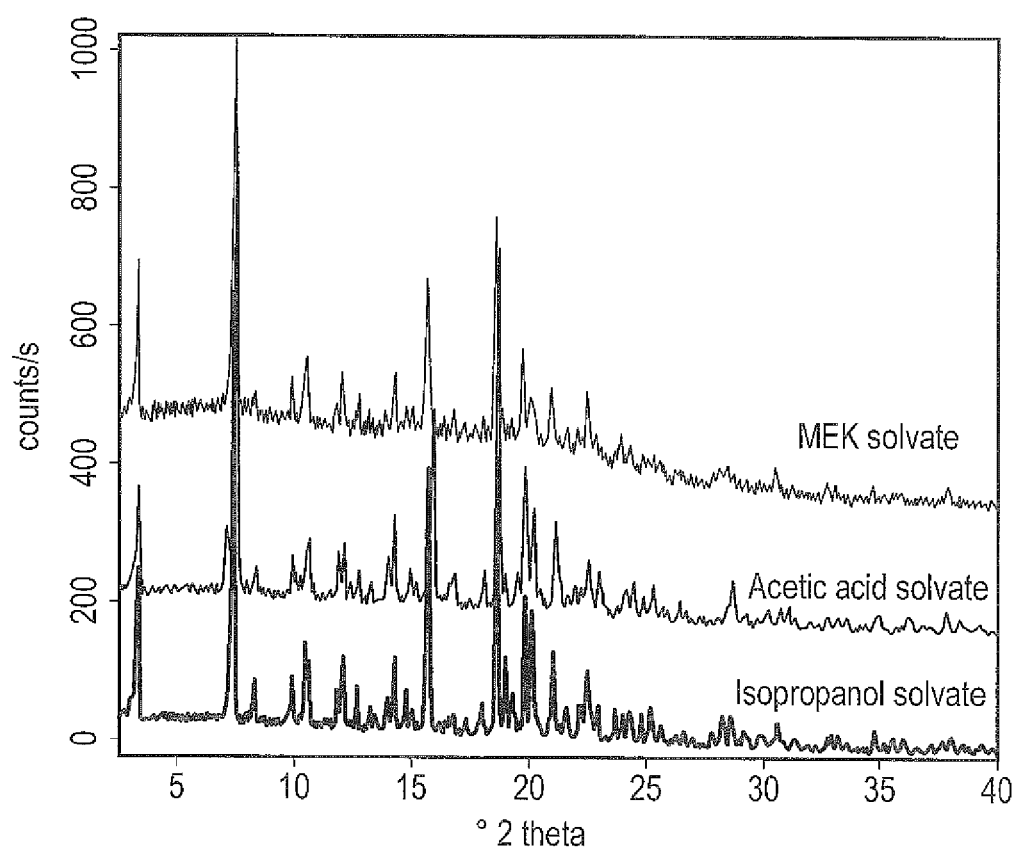

FIG. 11: Comparison of XRPDs of three polymorphs according to the present invention.

SUMMARY OF THE INVENTION

The present invention concerns new polymorphs or solid states of Tiacumicin B. The new polymorphs and new solid states are alternatives to the existing polymorphs.

In one aspect, the present polymorph is a crystal solvate of Tiacumicin B selected from the propanol crystal solvate, the acetic acid crystal solvate, the chlorobenzene crystal solvate, the methyl-ethyl-ketone crystal solvate, the isopropyl-acetate solvate or the isopropanol crystal solvate.

In one aspect, the present polymorph is a crystal solvate of Tiacumicin B selected from the propanol crystal solvate, the acetic acid crystal solvate, the chlorobenzene crystal solvate, the methyl-ethyl-ketone crystal solvate, the isopropyl-acetate solvate or the isopropanol crystal solvate characterized by a XRPD displaying a peak at diffraction angle 2θ of 19.9±0.1

In one aspect, the present polymorph is a crystal solvate of Tiacumicin B selected from the propanol crystal solvate, the acetic acid crystal solvate, the methyl-ethyl-ketone crystal solvate, the isopropyl-acetate solvate or the isopropanol crystal solvate characterized by a XRPD displaying a peak at diffraction angle 2θ of 3.3 and 19.9±0.1

In one aspect, the present polymorph is a crystal solvate of Tiacumicin B selected from the propanol crystal solvate, the acetic acid crystal solvate or the methyl-ethyl-ketone crystal solvate characterized by a XRPD displaying a peak at diffraction angle 2θ of 3.3 and 19.9±0.1

In one aspect, the n-propanol crystal solvate of Tiacumicin B is characterized by a XRPD displaying peaks at diffraction angles 2θ of 3.3, 7.5, 7.7, 18.8 and 19.9

In one preferred aspect, the acetic acid crystal solvate of Tiacumicin B is characterized by a XRPD displaying peaks at diffraction angles 2θ of 6.7, 7.6, 18.7 and 19.9

In one aspect, the chlorobenzene crystal solvate of Tiacumicin B is characterized by a XRPD displaying peaks at diffraction angles 2θ of 6.7, 18.8 and 19.9

In one preferred aspect, the methyl-ethyl-ketone crystal solvate of Tiacumicin B is characterized by a XRPD displaying peaks at diffraction angles 2θ of 3.3, 7.5, 15.7 and 18.6

In one preferred aspect, the isopropanol crystal solvate of Tiacumicin B is characterized by a XRPD displaying peaks at diffraction angles 2θ of 6.5, 9.9, 18.6 and 19.8

In one aspect of the present invention, the new solid state is a high purity amorphous Tiacumicin B material.

In one aspect of the present invention, the new solid state is a high purity amorphous Tiacumicin B material with a Tg of ca 113° C. as measured by DSC.

In one aspect of the present invention, the new solid state is a high purity amorphous Tiacumicin B material comprising less than 5% w/w water.

In one aspect of the present invention, the new solid state is a high purity amorphous Tiacumicin B material comprising less than 2% w/w water.

In one aspect of the present invention, the new solid state is a high purity amorphous Tiacumicin B material comprising less than 0.5% w/w water.

In one aspect of the present invention, the new solid state is a high purity amorphous Tiacumicin B material suitable for storage, comprising less than 2% w/w water and has a Tg of ca 113° C. as measured by DSC.

In one aspect of the present invention, the new solid state is a high purity amorphous Tiacumicin B material comprising more than 98% Tiacumicin B as measured by HPLC, which is suitable for storage and comprises less than 2% w/w water and has a Tg of ca 113° C. as measured by DSC.

In one aspect of the present invention, a new polymorph of Tiacumicin B is provided which is suitable for storage and displays XRPD with peaks at diffraction angles 2θ of 16.6 and 19.9±0.1

In one aspect of the present invention, the new polymorph of Tiacumicin B is an acetic acid solvate which is suitable for storage and displays XRPD with peaks at diffraction angles 2θ of 7.1, 16.6, 18.7 and 19.9±0.1

Figure 8A:
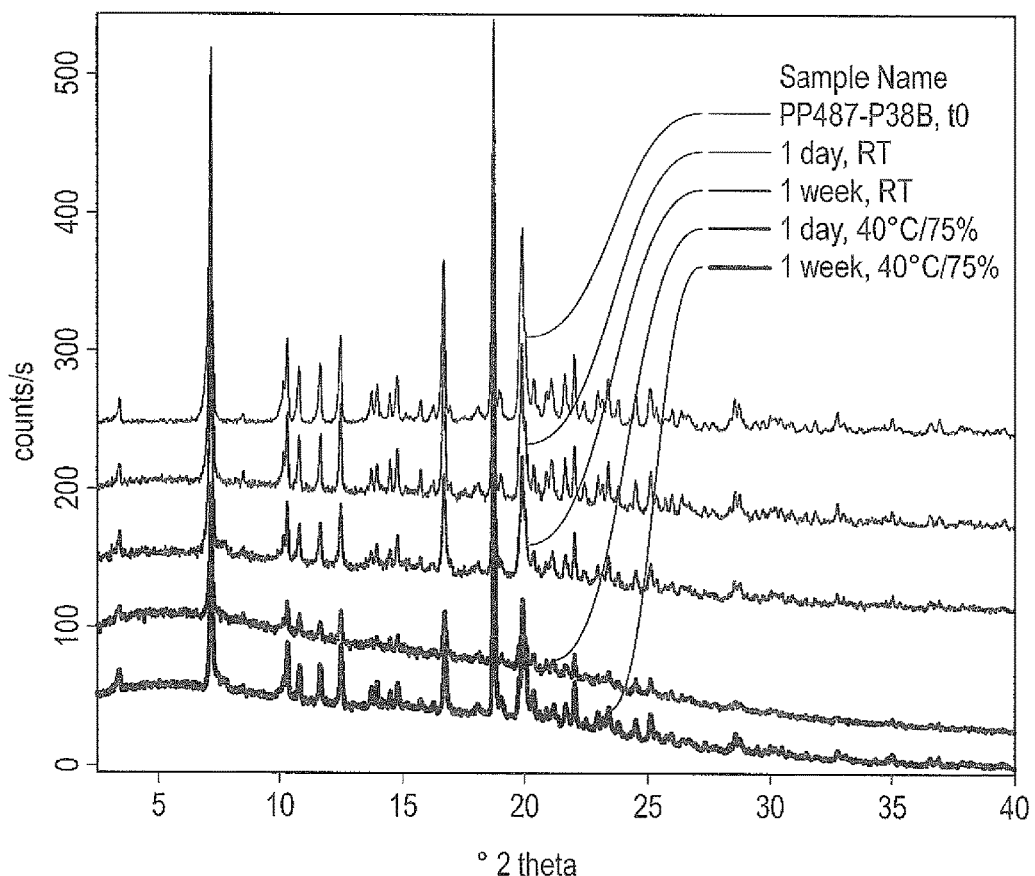
FIG. 8A: XRPD of the Tiacumicin solvate form a during storage.
Figure 8B:
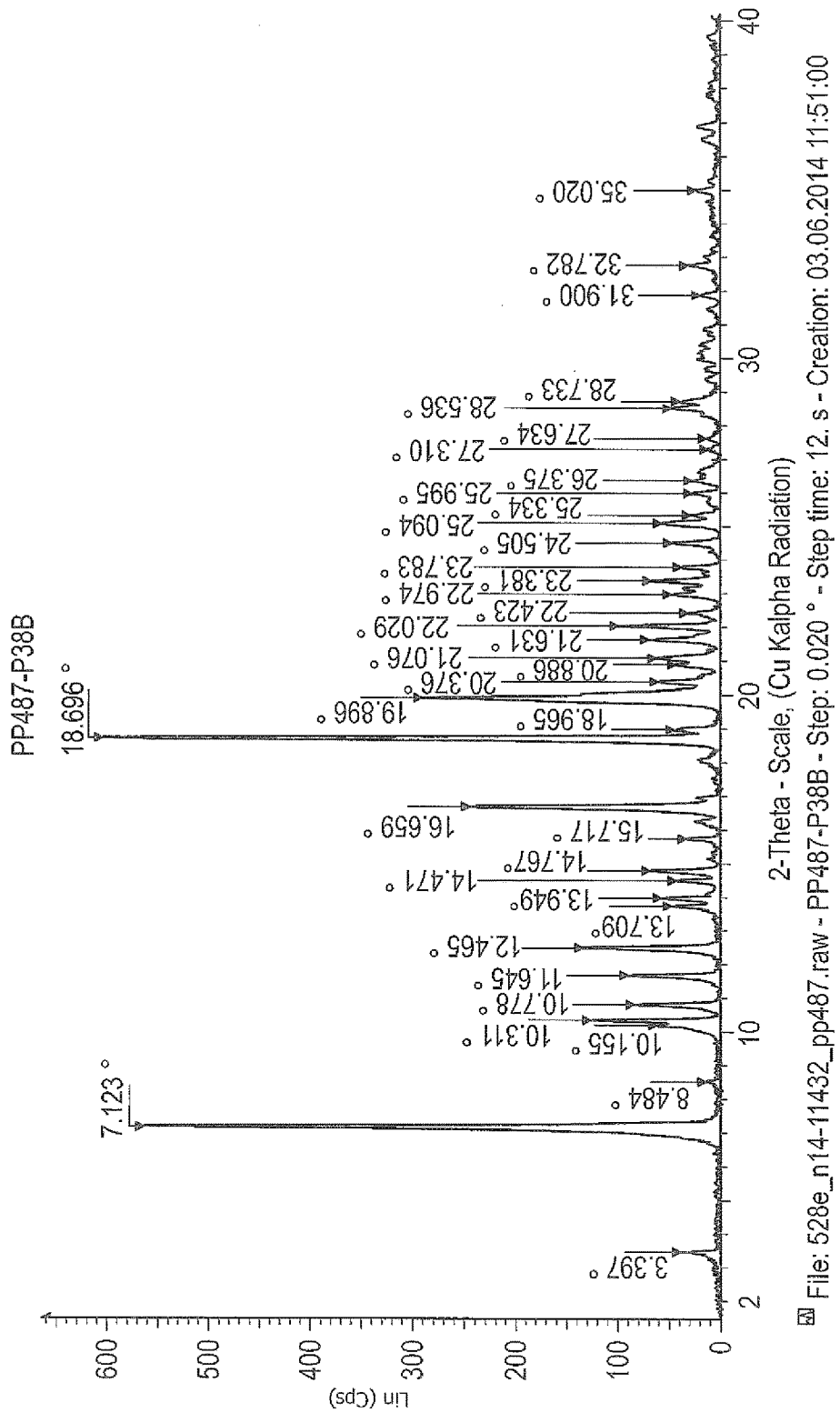
FIG. 8B: XRPD of the Tiacumicin solvate form a with peaks assigned with 2θ values.

In one aspect of the present invention, the new polymorph of Tiacumicin B is an acetic acid solvate which is suitable for storage and displays XRPD with peaks at diffraction angles 2θ of 7.1, 16.6, 18.7 and 19.9±0.1 substantially as shown in FIG. 8B. This form is called Tiacumicin solvate Form α.

In one aspect of the present invention, the new polymorph of Tiacumicin B is an isopropyl-acetate solvate which is suitable for storage and displays XRPD with peaks at diffraction angles 2θ of 7.3, 15.7, 16.6, 18.8, 19.9 and 20.2±0.1

Figure 9A:
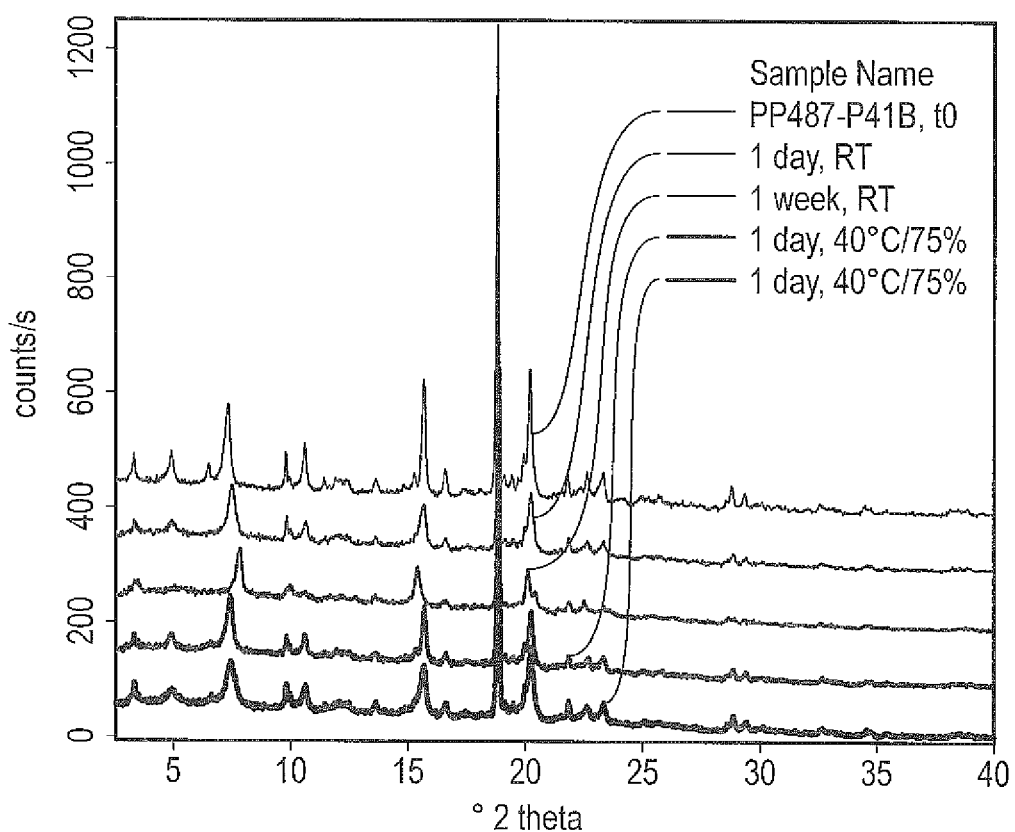
FIG. 9A: XRPD of the Tiacumicin solvate form β during storage.
Figure 9B:
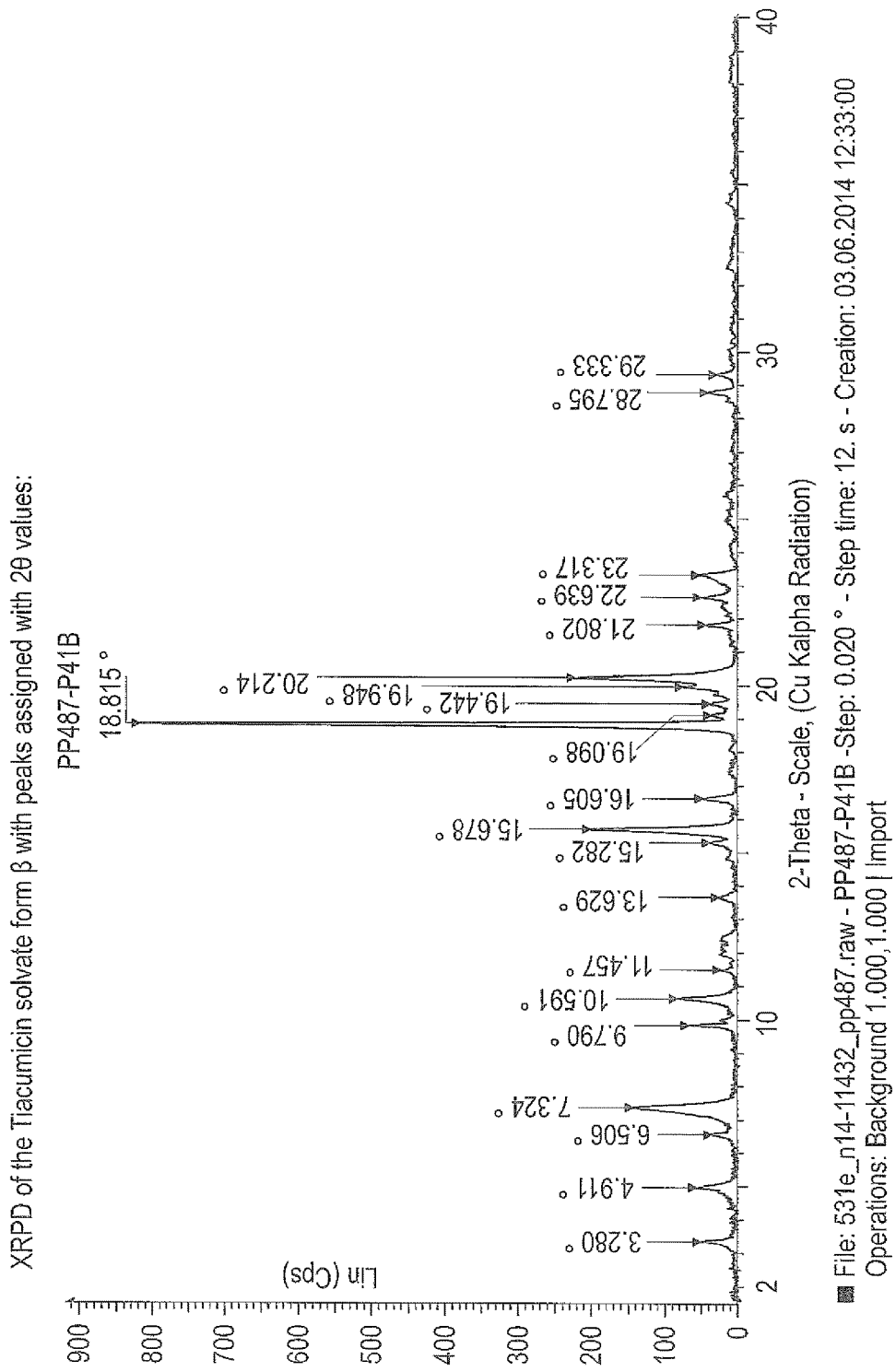
FIG. 9B: XRPD of the Tiacumicin solvate form β with peaks assigned with 2θ values.
Figure 10:
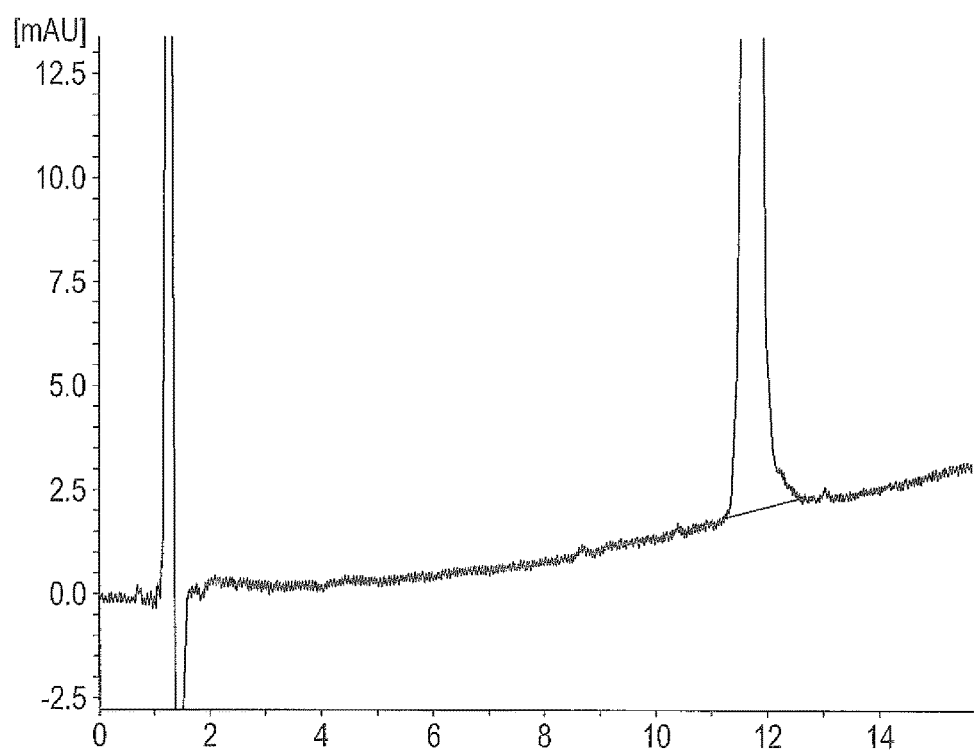
FIG. 10: Chromatogram of high purity Tiacumicin material.

In one aspect of the present invention, the new polymorph of Tiacumicin B is an isopropyl-acetate solvate which is suitable for storage and displays XRPD with peaks at diffraction angles 2θ of 7.3, 15.7, 16.6, 18.8, 19.9 and 20.2±0.1 substantially as shown in FIG. 9B. This form is called Tiacumicin solvate Form β.

In one aspect of the present invention, a new polymorph of Tiacumicin B is provided which is suitable for storage and displays XRPD with peaks at diffraction angles 2θ of 16.6, 18.8 and 19.9±0.1

In one aspect, the present polymorph is any crystal solvate of Tiacumicin B characterized by a XRPD displaying a peak at diffraction angle 2θ of 3.3, 9.9 and 18.6±0.1 or substantially as shown in FIG. 11.

The various aspects and more of the present invention, including various embodiments, will be described in further detail, with reference to the detailed description, examples and appended drawings.

DETAILED DESCRIPTION OF THE INVENTION

According to one embodiment, Tiacumicin B can be produced by fermentation of Dactylosporangium aurantiacum subspecies hamdenensis NRRL 18085 or Actinoplanes deccanensis ATCC 21983.

The term "polymorph" as used herein is meant to embrace crystalline solid states of a pure compound including solvates, co-crystals and crystals.

A "pure compound" as used herein is meant to cover compounds with a HPLC purity of at least 95%, or more preferred at least 97% and even more preferred at least 99%.

A "crystal solvate" as used herein is meant to cover polymorphs comprising a significant amount of a solvent relative to the pure compound. By "significant amount of a solvent relative to the pure compound" we mean a molar ratio of solvent:compound from 1:2 or more.

Tiacumicin B is meant to cover the compound represented by the following structure:

The term "XRPD" is meant to embrace any method using X-rays for obtaining a diffraction pattern of a solid state material. E.g. a method employing copper Kα radiation wavelength 1.54 Å. The methods used herein are described in more detail in the experimental part.

A "peak" as used herein concerning XRPD is a relatively sharp rise and fall of the signal between two 2θ values separated by a maximum of 2 degrees. Most peaks in the XRPDs herein have a relatively sharp rise and fall of the signal between two 2θ values separated by 1 degree or less.

A peak at a specific 2θ value is to be understood as a peak displaying the highest intensity at this value±0.1 degrees. A crystal solvate displaying peaks at 2θ values x, y and z±0.1 means that the pertaining XRPD comprises peaks at x±0.1, y±0.1 and z±0.1.

Amorphous Tiacumicin B can be obtained from solutions comprising dissolved Tiacumicin B by a variety of methods well known to the skilled person. E.g adding in an anti-solvent followed by solvent removal, sudden cooling of a saturated solution, freeze drying/lyophilization of the solutions, spray drying of the solutions etc.

Solutions comprising dissolved Tiacumicin B can be obtained by dissolving Tiacumicin B of any solid state or by purification of a fermentation broth from Dactylosporangium aurantiacum subspecies hamdenensis NRRL 18085 or Actinoplanes deccanensis ATCC 21983.

A "high purity amorphous Tiacumicin material" is a material comprising 97% or more of Tiacumicin B as measured by HPLC and displays a XRPD without any peaks. It can be obtained as described in Example 1.

Figure 7A:
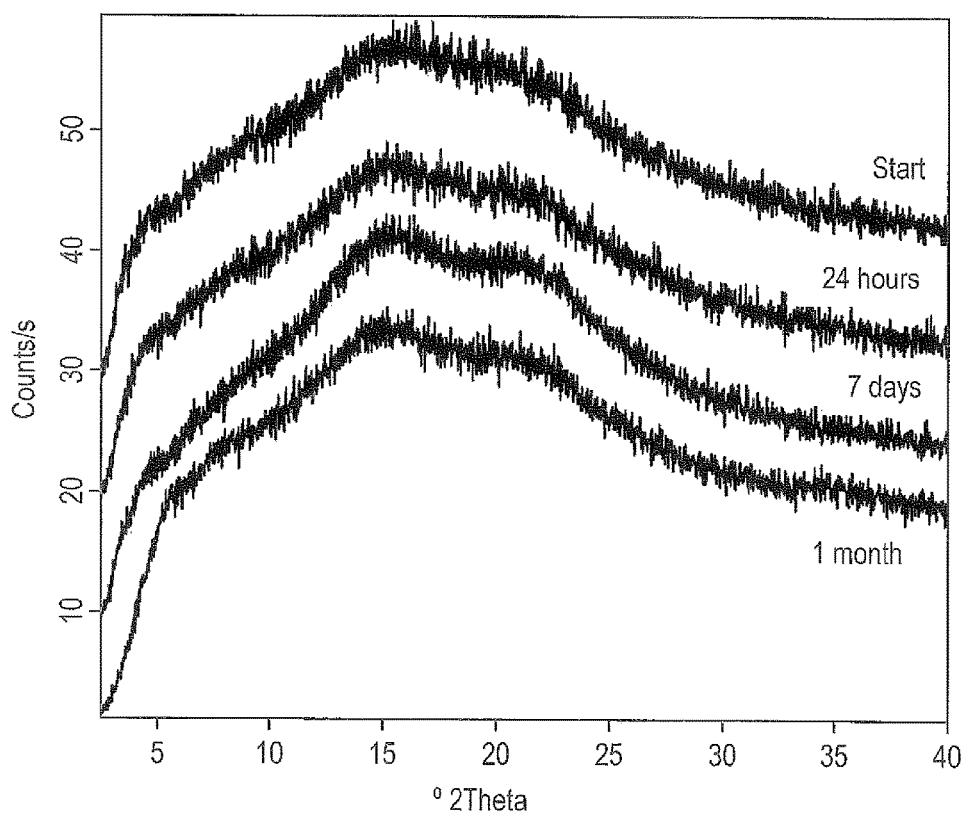
FIG. 7A: XRPD of high purity amorphous Tiacumicin material stored at 0 days (top), 1 day (middle) and 7 days (bottom).
Figure 7B:
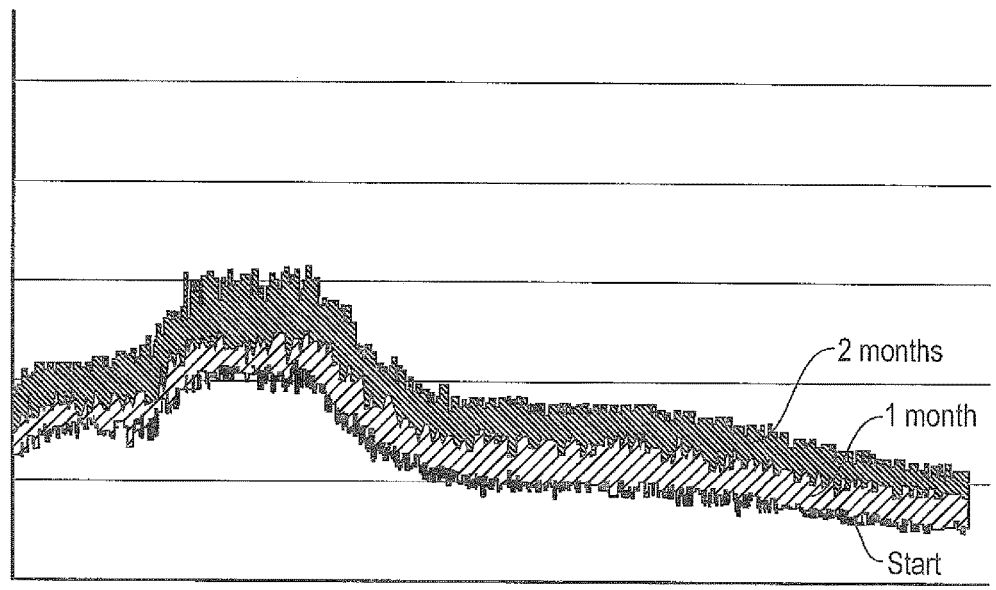
FIG. 7B: XRPD of high purity amorphous Tiacumicin material stored at 0 months (bottom), 1 month (middle) and 2 months (top).
Figure 7C:
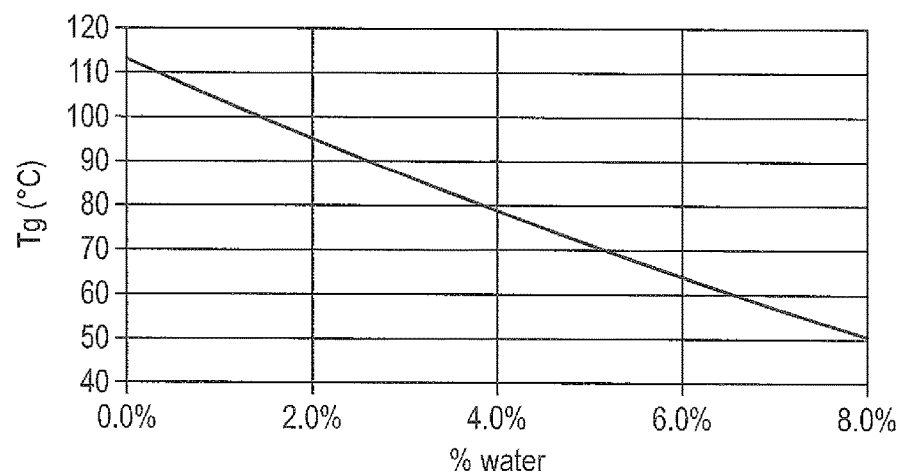
FIG. 7C: Glass transition temperature of high purity amorphous Tiacumicin material by using Fox Equation.

The high purity amorphous Tiacumicin material is hygroscopic with near linear water uptake (see FIG. 7C), but it's not deliquescent. The high purity amorphous Tiacumicin material is suitable for storage as demonstrated in example 7 or even longer-term storage. Thus the high purity amorphous Tiacumicin material is relatively stable with respect to crystallization and suitable for long-term storage (e.g storage for 3 months, 6 months, 9 months etc.).

A "crystal solvate of Tiacumicin B" is any crystal solvate comprising pure Ticaumicin B.

Pure Tiacumicin B as used herein is meant to cover Tiacumicin B with a HPLC purity of at least 95%, or more preferred at least 97% and even more preferred at least 99% by detection at 230 nm.

Tiacumicin B can be produced as disclosed in the prior art but is also commercially available (e.g. Bioaustralis Fine Chemicals). The crystalline Tiacumicin B starting material is also commercially available (e.g Brightgene Bio-MedicalTechnology).

Experimental Data:

XRPD Methods:

Stoe Stadi P; Mythen1K Detector; Cu-Kα1 radiation; standard measurement conditions: transmission; 40 kV and 40 mA tube power; curved Ge monochromator; 0.02°2θ step size, 12 s step time, 1.5-50.5°2θ scanning range; detector mode: step scan; 1°2θ detector step; standard sample preparation: 10 to 20 mg sample was placed between two acetate foils; sample holder: Stoe transmission sample holder; the sample was rotated during the measurement. Filenames of patterns recorded on this instrument consist of a three-digit number followed by a letter.

or

Bruker D8; Copper $K_a$ radiation, 40 kV/40 mA; LynxEye detector, 0.02°2θ step size, 37 s step time.

Sample Preparation

The samples were generally measured without any special treatment other than the application of slight pressure to get a flat surface. Silicon single crystal sample holder types: a) standard holder for polymorphism screening, 0.1 mm deep, less than 20 mg sample required; b) 0.5 mm deep, 12 mm cavity diameter for c. 40 mg; c) 1.0 mm deep, 12 mm cavity diameter for c. 80 mg. All samples measured on the Bruker D8 are rotated during the measurement.

Example 1: Amorphous Tiacumicin B

Crystalline Tiacumicin B starting material (see XRPD in FIG. 1A) with a HPLC purity of ca 99% and a water content of less than 1% w/w was dissolved in water/THF (5:1, v:v) and lyophilized. The lyophilized product was amorphous (see FIG. 1B).

Example 2: Chlorobenzene Crystal Solvate of Tiacumicin B

Amorphous Tiacumicin B obtained in example 1 (69 mg) was mixed with 1.5 ml n-heptane/chlorobenzene 1:2 (v:v). The suspension was shaken at r.t. for 24 hours. Finally, 50% of the solvents were evaporated at r.t. under gentle $N_2$ flow (no flow control). The resulting solid was filtered off. The wet material thus obtained comprised 23% w/w chlorobenzene as measured by TG-FTIR. XRPD of the chlorobenzene crystal solvate of Tiacumicin B is shown in FIGS. 2A and 2B.

Example 3: n-Propanol Crystal Solvate of Tiacumicin B

Amorphous Tiacumicin B obtained in example 1 (100 mg) was mixed 2 ml n-propanol to form a slurry. The suspension was stirred at r.t. for 24 hours. Finally, the solvent was evaporated at r.t. under gentle $N_2$ flow. The wet material obtained comprised 4% w/w n-propanol as measured by TG-FTIR. XRPD of the n-propanol crystal solvate of Tiacumicin B is shown in FIGS. 3A and 3B.

Example 4: Iso-Propanol Crystal Solvate of Tiacumicin B

Amorphous Tiacumicin B obtained in example 1 (73 mg) was mixed with 1.5 ml iso-propanol to form a slurry. The suspension was shaken at r.t. for 24 hours. Finally, 50% of the solvents were evaporated at r.t. under gentle $N_2$ flow. The slurry was then filtered and the wet material obtained comprised 17% w/w iso-propanol as measured by TG-FTIR. The isopropanol was lost in two steps; first 11% w/w and then 6% w/w.

XRPD of the iso-propanol crystal solvate of Tiacumicin B is shown in FIGS. 4A and 4B.

Example 5: Methyl-Ethyl-Ketone (MEK) Crystal Solvate of Tiacumicin B

Amorphous Tiacumicin B obtained in example 1 (71 mg) was mixed with 1.5 ml n-heptane/MEK 1:2 (v:v). The suspension was shaken at r.t. for 24 hours. Finally, 50% of the solvents were evaporated at r.t. under gentle $N_2$ flow (no flow control). The resulting solid was filtered off. The wet material obtained comprised 6% iso-propanol as measured by TG-FTIR. XRPD of the methyl-ethyl-ketone crystal solvate of Tiacumicin B is shown in FIGS. 5A and 5B.

Example 6: Acetic Acid Crystal Solvate of Tiacumicin B

Crystalline Tiacumicin B starting material (100 mg) with a HPLC purity of ca 99% and a water content of less than 1% w/w was mixed with 2 ml water/acetic acid (1:1, v:v) to form a slurry. The suspension was stirred at r.t. for 48 hours. Finally, the solvents were evaporated at r.t. under gentle $N_2$ flow. The obtained material comprised 6% w/w acetic acid as measured by TG-FTIR. XRPD of the acetic acid crystal solvate of Tiacumicin B is shown in FIGS. 6A and 6B.

Example 7: Stability of High Purity Amorphous Tiacumicin Material

Several samples of high purity amorphous Tiacumicin B material were stored at 40° C./75% relative humidity. XRPDs obtained at start, 24 hours, 7 days and 1 month show amorphous material (se FIG. 7A).

Several samples of high purity amorphous Tiacumicin B material were stored at room temperature under normal light conditions. XRPDs obtained at start, 1 month and 2 months show amorphous material (se FIG. 7B). XRPDs of high purity amorphous Tiacumicin B material also show amorphous material at 3 months.

Example 8: Crystal Solvate of Tiacumicin B (Form α)

Crystalline Tiacumicin B starting material (220 mg) with a HPLC purity of ca 99% and a water content of less than 1% w/w was mixed with 4.5 ml water/acetic acid (1:1, v:v) to form a slurry. The suspension was stirred at r.t. for 96 hours. Finally, the resulting solid was filtered off and dried in air (5 min).

The obtained material comprised 16% w/w acetic acid as measured by TG-FTIR. XRPD of the storage suitable form α of Tiacumicin B is shown in FIG. 8A. XRPD of the storage suitable form α of Tiacumicin B with peaks assigned with 2θ values is shown in FIG. 8B. XRPD of the storage suitable form α of Tiacumicin B in table format of is shown in FIG. 8C.

Example 9: Crystal Solvate of Tiacumicin B (form (β)

Crystalline Tiacumicin B starting material (100 mg) with a HPLC purity of ca 99% and a water content of less than 1% w/w was mixed with isopropyl-acetate (1:1, v:v) to form a slurry. The suspension was stirred at r.t. for 48 hours. Finally, the solvents were evaporated at r.t. under gentle $N_2$ flow. Crystalline Tiacumicin B starting material (220 mg) with a HPLC purity of ca 99% and a water content of less than 1% w/w was mixed with 3 ml isopropyl acetate (most solid dissolved) and 3 ml n-heptane to form a slurry. The suspension was stirred at r.t. for 96 hours. Finally, the resulting solid was filtered off and dried in air (5 min).

The obtained material comprised 9% w/w isopropylacetate as measured by TG-FTIR. XRPD of the storage suitable form β of Tiacumicin B is shown in FIG. 9A. XRPD of the storage suitable form β of Tiacumicin B with peaks assigned with 2θ values is shown in FIG. 9B. XRPD of the storage suitable form β of Tiacumicin B in table format of is shown in FIG. 9C.

Figure 1A:
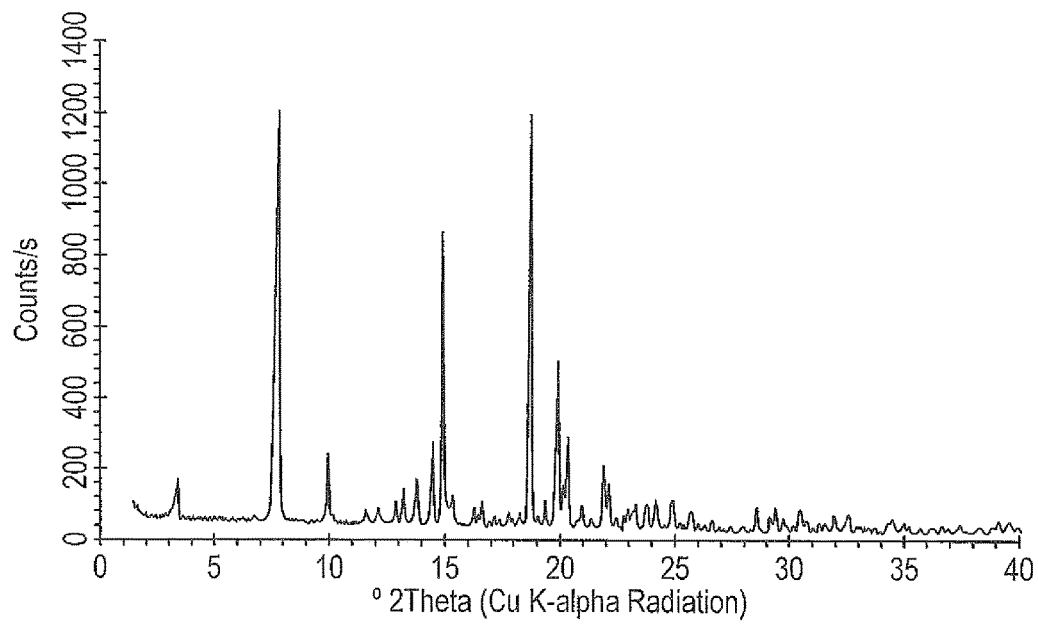
FIG. 1A: Graphical XRPD of the Tiacumicin B starting material
Figure 1B:
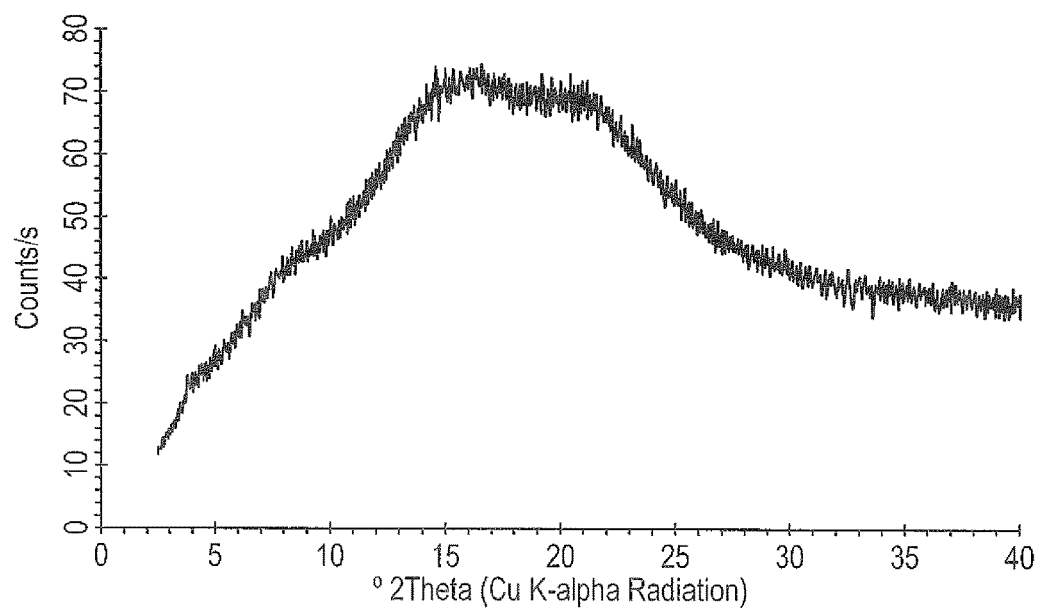
FIG. 1B: Graphical XRPD of the amorphous Tiacumicin B material
Figure 2A:
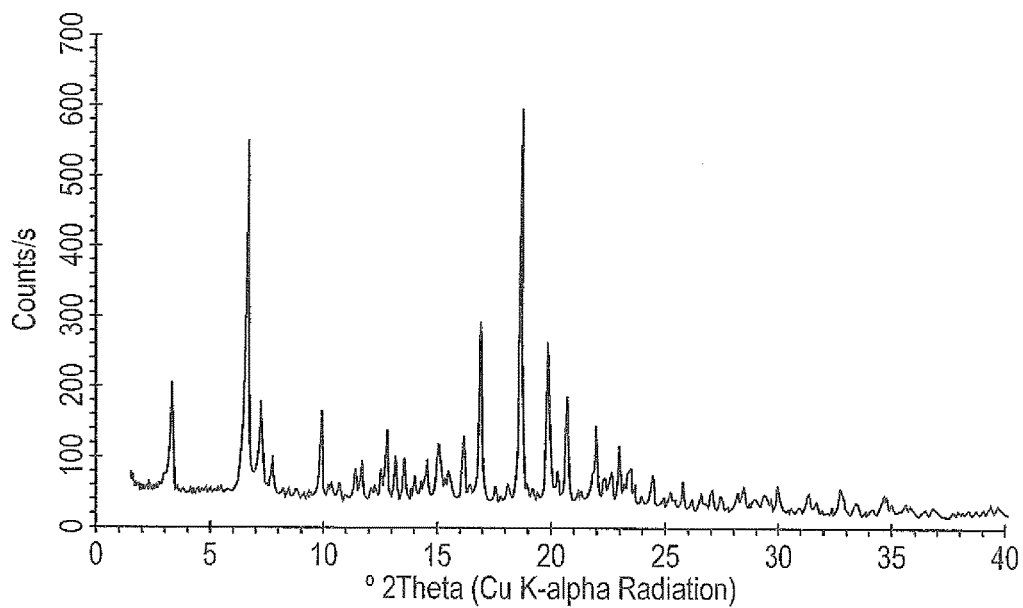
FIG. 2A: Graphical XRPD of the chlorobenzene crystal solvate of Tiacumicin B
Figure 3A:
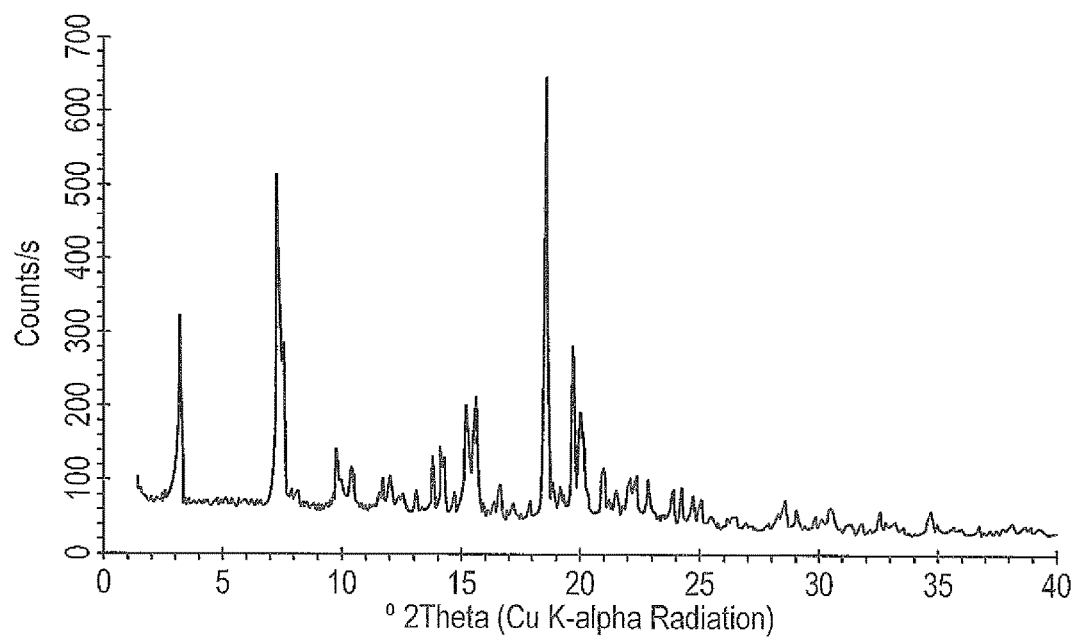
FIG. 3A: XRPD of the n-propanol crystal solvate of Tiacumicin B
Figure 4A:
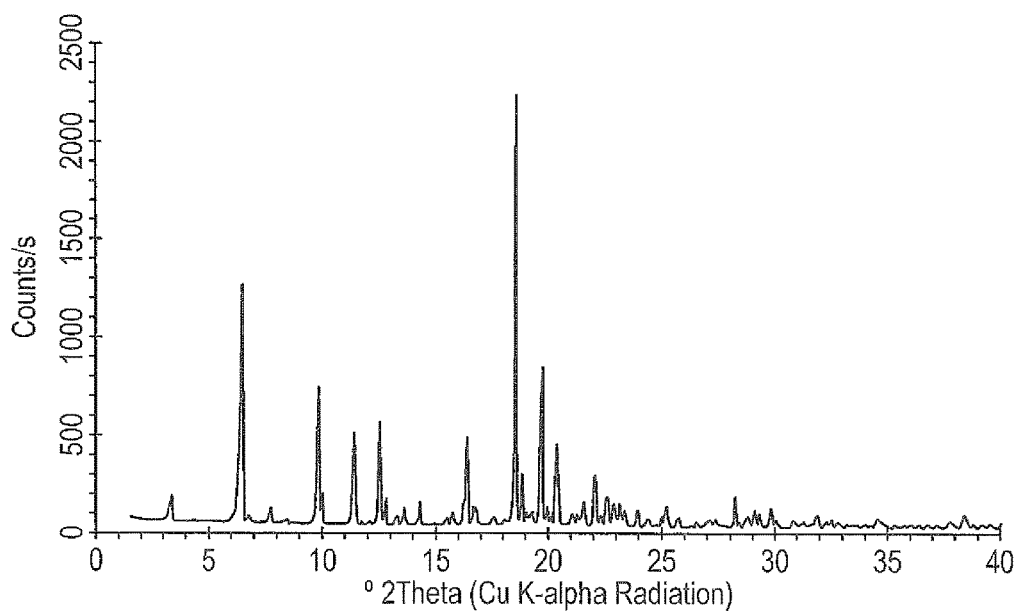
FIG. 4A: Graphical XRPD of the isopropanol crystal solvate of Tiacumicin B
Figure 5A:
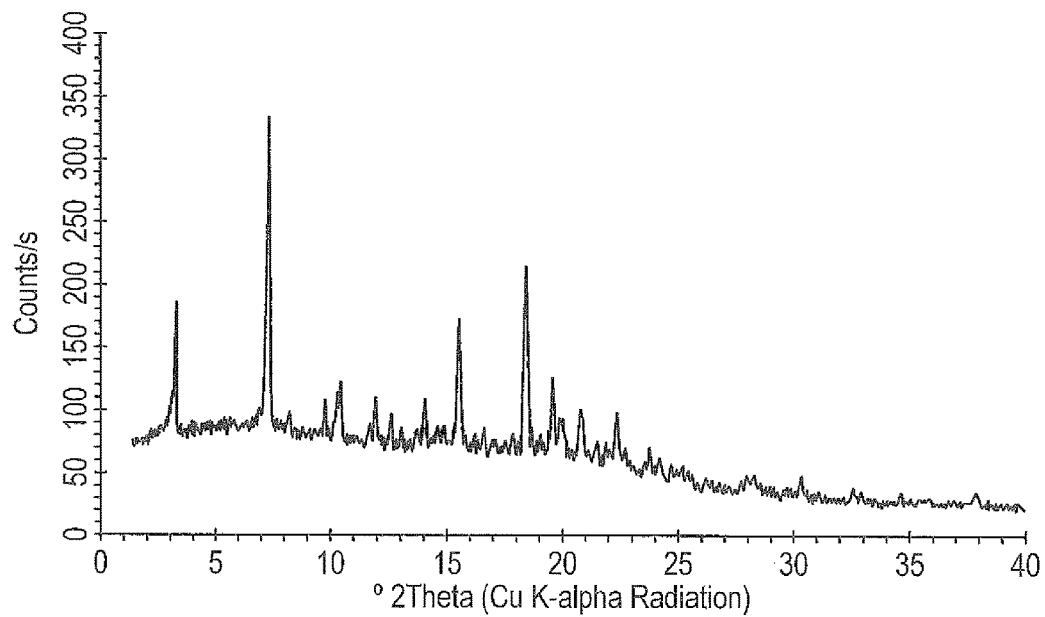
FIG. 5A: Graphical XRPD of the methyl-ethyl-ketone crystal solvate of Tiacumicin B.
Figure 6A:
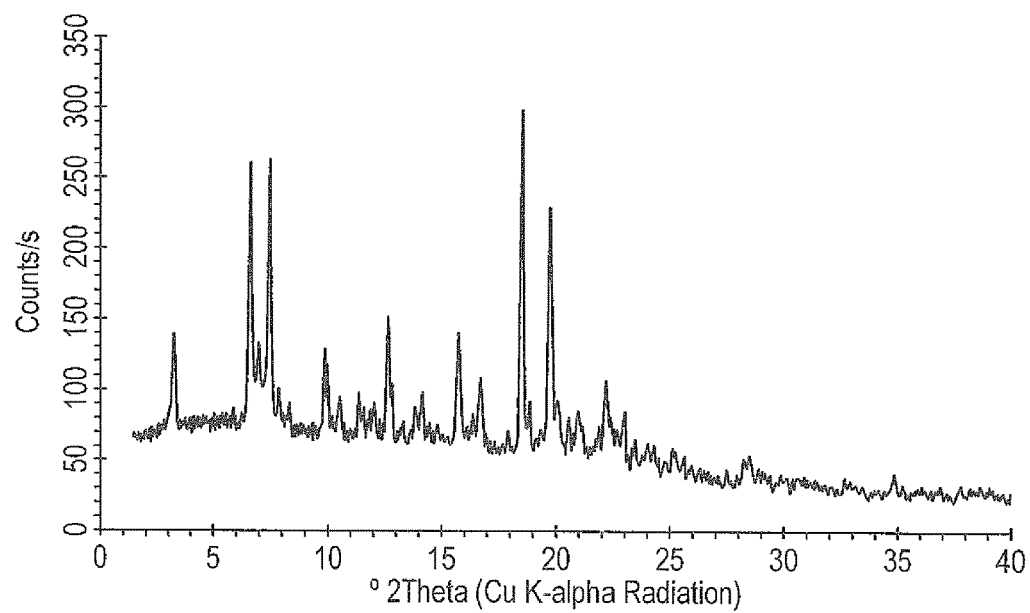
FIG. 6A: Graphical XRPD of the acetic acid crystal solvate of Tiacumicin B

The invention claimed is:
1. A crystal solvate of Tiacumicin B selected from
   the n-propanol crystal solvate substantially as shown in FIG. 3A,
   the acetic acid crystal solvate substantially as shown in FIG. 11,
   the chlorobenzene crystal solvate substantially as shown in FIG. 2A,
   the methyl-ethyl-ketone crystal solvate substantially as shown in FIG. 11,
   the isopropyl-acetate solvate substantially as shown in FIG. 9B and
   the isopropanol crystal solvate substantially as shown in FIG. 11.
2. An acetic acid crystal solvate of Tiacumicin B characterized by a XRPD substantially as shown in FIG. 11.

\* \* \* \* \*